Figure 1:
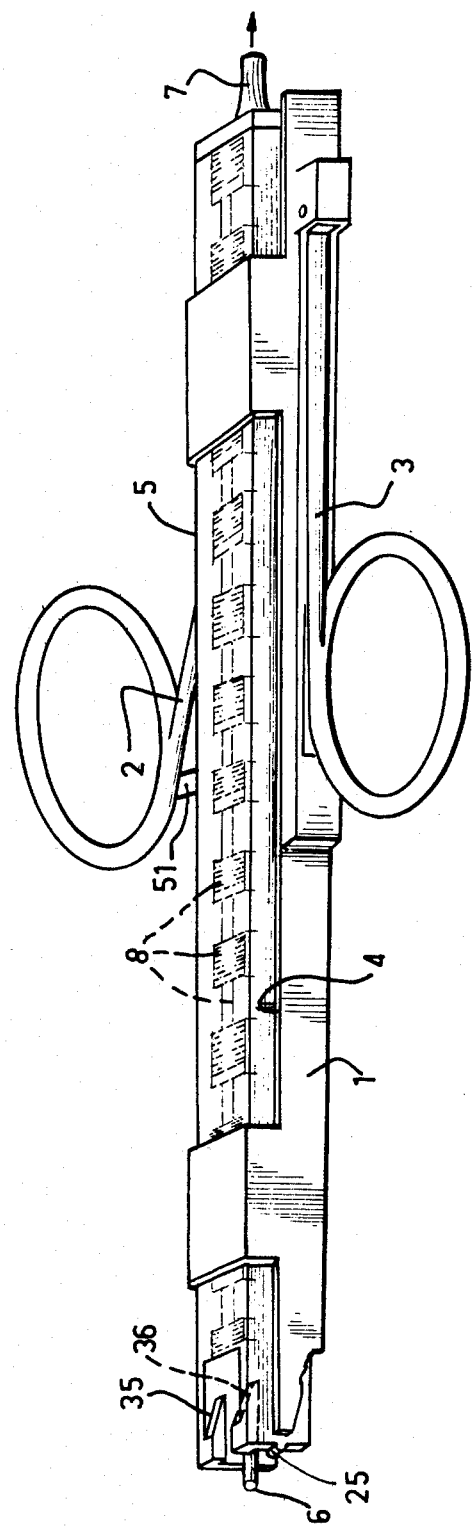

United States Patent [19]

Périssé

[11] 4,050,465
[45] Sept. 27, 1977

[54] AUTOMATIC SURGICAL APPARATUS FOR LIGUTARING BLOOD VESSELS

[76] Inventor: Pierre Périssé, 8 rue du Strade, 31370 Rieumes, France

[21] Appl. No.: 665,900

[22] Filed: Mar. 11, 1976

[30] Foreign Application Priority Data

Mar. 14, 1975 France .............................. 74.08039

[51] Int. Cl.² .......................................... A61B 17/12
[52] U.S. Cl. ............................................... 128/326
[58] Field of Search ................... 128/326 R; 222/236, 222/238; 289/18 R; 227/19 R

[56] References Cited

U.S. PATENT DOCUMENTS

| 1,400,653 | 12/1921 | Barbour | 128/326 |
| 3,665,924 | 5/1972 | Noiles et al. | 128/326 |

FOREIGN PATENT DOCUMENTS 2,229,377  12/1974  France ............................. 128/326

Primary Examiner—Robert W. Michell
Assistant Examiner—Henry J. Recla
Attorney, Agent, or Firm—J. Harold Nissen

[57] ABSTRACT

A surgical apparatus for ligature of cut blood vessels having the appearance of a hemostatic clip including a support and dispensing structure to receive a charger and a supply of cartridges each carrying a preformed knot. The charger is movably coupled to a movable member on the dispensing structure to dispense a plurality of knots one after the other. Adjacent cartridges are removably coupled to each other on the support and after dispensing of the knot, its cartridge is disposed of. The charger cooperates with the cartridge and reverse movements of the movable member to dispense the knot, tie it about the blood vessel, sever it and then dispose of the cartridge, and then place a new cartridge in place to repeat the dispensing of a knot.

7 Claims, 15 Drawing Figures

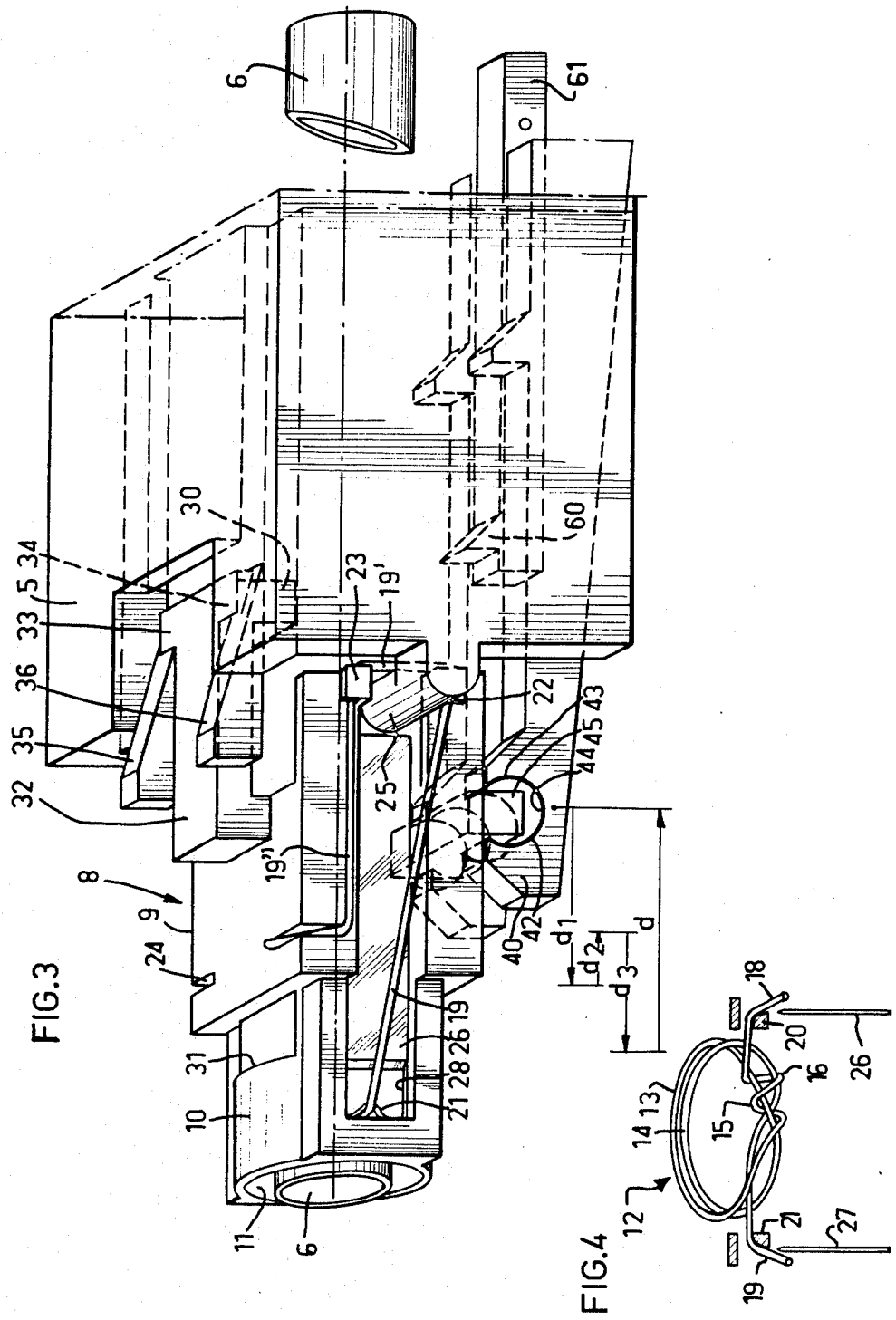

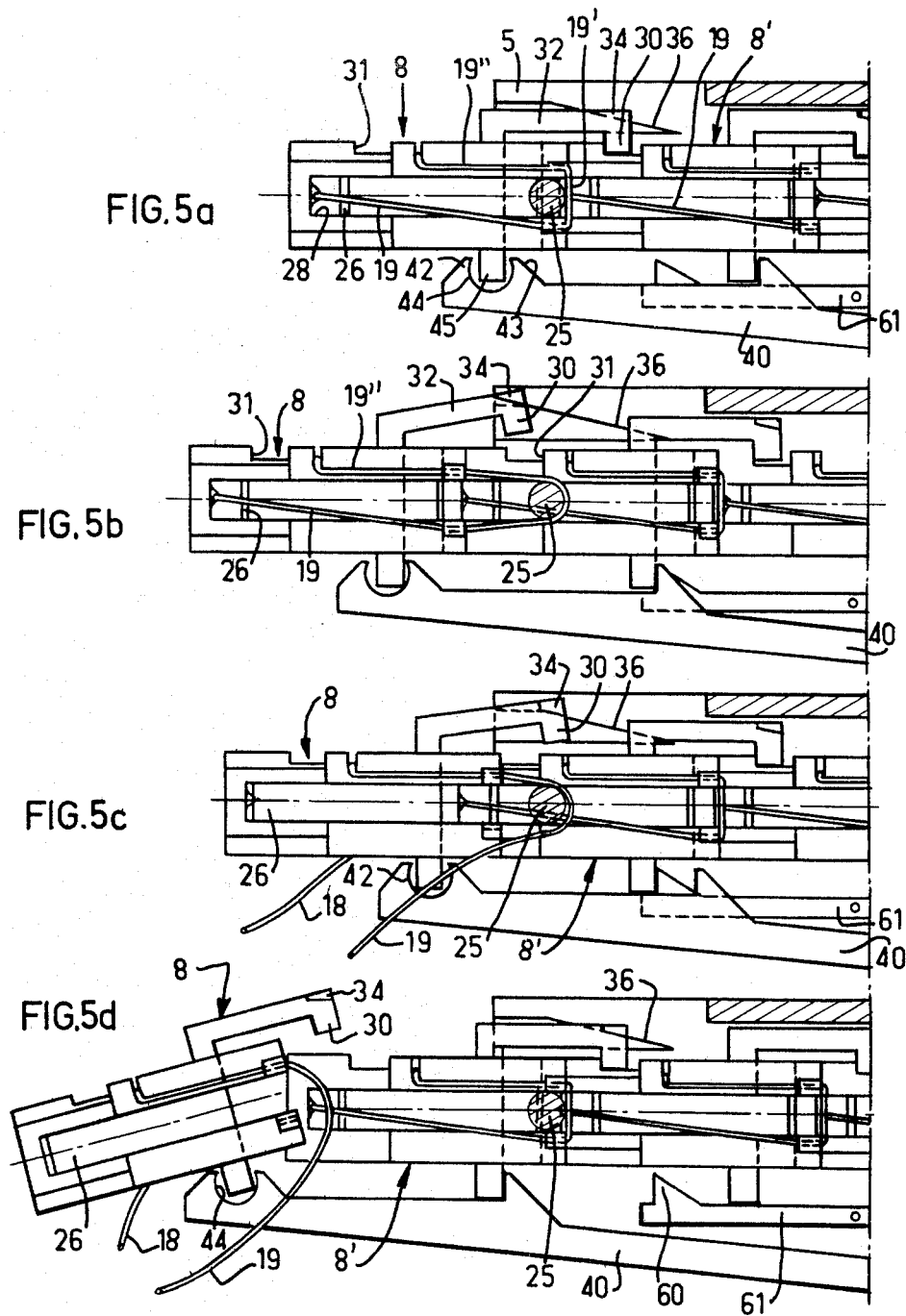

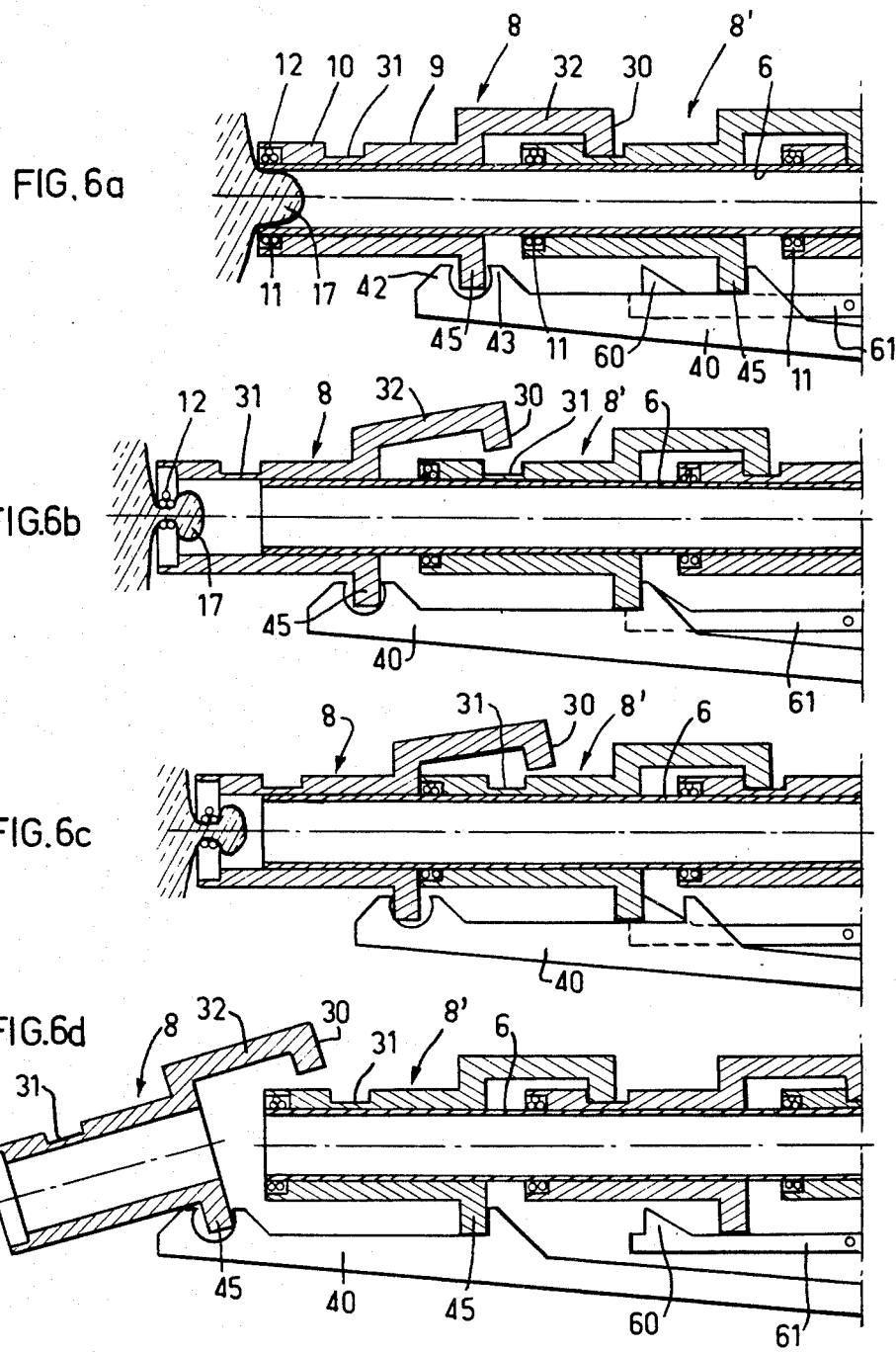

AUTOMATIC SURGICAL APPARATUS FOR LIGUTARING BLOOD VESSELS

The present invention concerns a surgical apparatus intended for repetitively and instantly making ligatures on blood vessels which are cut in the course of a surgical operation.

French Patent application No. 74.00717 filed on 9th January 1974 by the present applicant describes an apparatus capable of carrying out such a function. This apparatus is of elongate shape and is held in one hand in the manner of a pencil. It comprises a plurality of knot-carrier cartridges which are disposed one after the other in a charger and which are subjected as a group to the action of a spring which urges them towards the operating end of the apparatus. Each cartridge comprises two coaxial portions which can turn relative to each other, one portion carrying the knot proper and the other serving as an anchorage for the strands of the knot, means being provided for rotating the portion carrying the knot relative to the other portion, during the advance movement of the train of cartridges in the charger, thereby to tighten the knot.

This remainder of these few features of the known apparatus will firstly indicate the disadvantage of its particular shape, which runs the risk of being a serious handicap as regards adoption of the apparatus by surgeons. Surgeons generally use haemostatic clamps which are of a shape and a mode of operation completely different from those of the above-described apparatus.

On the other hand, because the train of cartridges is loaded by a spring, the thrust force which is applied to the cartridges reduces as the charger is emptied of cartridges, and it can even happen that the last cartridges remaining in the charger are subjected to such a small thrust force that they cannot be ejected.

Finally, the two-part cartridges are reasonably difficult to produce and are therefore burdensome.

The object of the present invention is to overcome these disadvantages by proposing an apparatus which is handled in the manner of the haemostatic clamp and in which the cartridges are of much simpler design than that of the cartridge of the above-mentioned patent application.

The apparatus according to the present invention is characterised in that it has substantially the appearance of a haemostatic clamp, that is to say, it comprises two arms with rings for receiving the fingers, which are pivoted on respective sides of an elongate support on which a tubular charger is removably fixed, the charger being filled with knot-carrier cartridges that are threaded with a small clearance onto a tubular shaft arranged co-axially in the charger and connected by its rearward end to a vacuum source by means of a flexible conduit so that a suction force will be created at its front end, each cartridge comprising a single tubular part which at its front end carries a preformed knot, which is initially loose, and whose strands extends radially in opposite directions, bear against deflection points on the cartridge, each defining a catching portion which is transverse with respect to the axial direction of the cartridge, and are fixed on an anchoring portion of the cartridge, each cartridge carrying two slidable blades for cutting the strands of the knot at the level of the radially directed portions, coupling means by which each cartridge is removably coupled to the preceding and the following cartridges so that the train of cartridges can be displaced as a group, and a heel which is intended to be caught, when the corresponding cartridge arrives at the front end of the charger, by gripping means that can be entrained by the above-mentioned arms, in an alternating longitudinal movement which is broken down into a first advance movement in the course of which disengagement means provided on the cartridge and at the front end of the charger disengage the first cartridge of the train, or the leading cartridge, from the following cartridge, and abutments which are also provided at the front end of the charger intercept the transverse catching portions of the strands, thereby tightening the knot, a first return movement of the leading cartridge so that its cutting blades come into abutment with the following cartridge and slide to cut the strands of the tightened knot, a second forward movement in the course of which the leading cartridge is expelled from the charger, and a second return movement at the end of which the apparatus returns to its initial condition, the second cartridge assuming the position of that which had been expelled.

The mechanism of the apparatus is so designed that, by actuating the arms in the manner in which the arms of a haemostatic clamp are actuated, that is to say, by moving them apart then by bringing them together, the leading cartridge is disconnected from the following cartridge, then entrained forwardly so that its knot is tightened, then entrained rearwardly into abutment against the following cartridge so that its blades cut the strands of the tightened knot, then ejected from the apparatus, and finally replaced by a fresh intact cartridge.

The invention will be described in detail with reference to the accompanying drawings, in which:

FIG. 1 is a perspective view of a particular embodiment of the apparatus according to the invention, FIGS. 2a to 2d are diagrammatic views of the actuating mechanism of the apparatus, the charger not being shown for the sake of clarity of the drawing, FIG. 3 is a perspective view on an enlarged scale of the end of the FIG. 1 construction, the charger being in position, FIG. 4 shows an embodiment of the knot used, FIG. 5a to 5d are elevational views of the apparatus with charger, in the four positions corresponding to those shown in FIGS. 2a to 2d, and FIGS. 6a to 6d are views in axial cross-section of the apparatus with charger, in the four positions corresponding to FIGS. 2a to 2d.

The surgical apparatus according to the invention, as shown in FIG. 1, has the general shape of a haemostatic clamp. It comprises an elongate body 1 on which are pivoted two actuating arms 2, 3, each of which is provided with a ring for introducing the fingers. Actuation of the arms 2, 3 is substantially comparable to the actuation of the arms of a haemostatic clamp, so that the user of the this apparatus is accustomed thereto virtually instantly.

The body comprises a longitudinal slide 4 in which is introduced a tubular charger 5. Once the tubular charger 5 is in place, it can be locked in the body, for example by a pawl-like locking action. Likewise, the charger can be released from the body, then separated from the body, by sliding it out of the slide 4. The charger contains a coaxial tubular shaft 6 which is connected to an end member 7 secured to the rear end of the charger. The end member 7 is connected to a vacuum source, by way of a flexible conduit (not shown). In this way a permanent suction force is created at the forward end of the shaft 6, to the left in FIG. 1.

Threaded onto the shaft 6 are a plurality of knot-carrying cartridges 8 which are each connected one to the other so as to form a train of cartridges which can be displaced as a group. FIG. 3 shows the cartridge which is at the head of the train i.e., the leading cartridge, but all the cartridges are of the same structure, as FIGS. 6a to 6d also show. Each of the cartridges is so dimensioned that it can slide with a small clearance between the shaft 6 and the charger. Since the relative angular position of the cartridges and the charger is of importance as regards the operation of the apparatus, as will be described hereinafter, the cartridges and the charger will be of complementary non-circular sections, for example of square section. In this way the train of cartridges does not turn in the charger.

Referring to FIG. 3, each charger comprises a moulded part, for example of plastics material. It can be mass-produced, and can therefore be of low cost price, which makes it possible for it to be discarded after use. The cartridge comprises a body 9 and a forward part 10, in one piece. At the forward end of the forward part 10, the bore of the cartridge is enlarged, forming with the shaft 6 an annular housing 11 in which a preformed knot 12 is arranged (see also FIGS. 6a to 6b).

The knot can be of any type which permits forcible and irreversible gripping of the blood vessel to be ligatured. FIG. 4 shows by way of example a preferred type of knot. This knot comprises two gripping loops 13 and 14, and is prevented from becoming undone by means of two hitches 15 and 16. The two loops is avoid the danger, which can be found with single-loop knots, of cutting the bud-shaped portion of tissue 17 which is drawn into the interior of the tubular shaft 6 (FIG. 6b).

The strands 18 and 19 of the knot extend radially in opposite directions, turn about two deflection points 20, 21 which are diametrically opposed to each other, on the forward part 10, then about finger portions 22 and 23 which are moulded with the body 9, the strands finally being anchored in gripping notches 24 formed on the body 9. As shown in FIG. 3, between the finger portions 22 and 23 each strand has a portion, such as 19', which is transverse with respect to the axis of the charger.

At its forward end the charger comprises two internal abutments 25 which project into the path of the transverse portions such as 19'. Thus, if the cartridges are displaced towards the left in FIG. 3, the transverse portions are intercepted by the abutments 25 so that the strands 18 and 19 are tensioned and accordingly the knot 12 is tightened (see FIG. 5b).

Two cutting blades 26, 27 (FIGS. 3 and 4) are mounted slidably in two longitudinal slides 28 formed on the cartridge at the level of the deflection points 20, 21 for guiding the strands of the knot. Initially, the blades are in a retracted position, but, as will be described in detail hereinafter, after the knot has been tightened, the blades are capable of being urged towards the left in FIG. 3, by the rearward ends of the blades abutting against the following cartridge 8' of the train of cartridges.

As already explained, the cartridge are coupled each to the following cartridge. For this purpose, in accordance with the invention, each cartridge comprises a claw member 30 and a recess 31, the claw member of each cartridge engaging into the recess in the following cartridge, as is clearly shown in FIG. 6a. The claw member is advantageously carried at the end of an arm 32 which is moulded with the body 9 of the cartridge and connected thereto by a region which is of sufficiently small section to permit resilient flexing of the arm.

Means are provided for disengaging a leading cartridge 8 from the following cartridge 8'. In the embodiment illustrated, these disengagement means comprise on the one hand, on each cartridge, two lateral lugs 33 and 34 which are carried by the arm 32, and on the other hand, at the forward end of the charger, two ramp surfaces 35 and 36 which are inclined forwardly and upwardly and are capable of intercepting the lugs during the movement of the cartridge towards the left (FIG. 5a) and consequently, progressively lifting the arm 32 (FIGS. 5b and 6b); this disconnects the claw member 30 of the cartridge 8 from the recess 31 of the following cartridge 8'.

From the above description it will be noted that, in order to carry out a complete operating cycle, the leading cartridge 8 must first be urged towards the left (FIG. 5a) so as to effect simultaneously disengagement of the cartridge 8 from the following cartridge 8' and then tightening of the knot, and then towards the right (FIG. 5c) so as to cut the strands, and finally towards the left (FIG. 5d) to expel the used cartridge. All these movements can be imparted to the cartridges by means of the apparatus of FIG. 1, the mechanism of which will now be described with reference to FIGS. 2a to 2d and 5a to 5d.

The apparatus comprises a longitudinal member 40 which is mounted slidably in a longitudinal guide groove formed in the bottom of the slide 4 (FIG. 1). The longitudinal member 40 is terminated at the level of the forward end of the charger 5 by a gripping portion comprising two hooks 42 and 43 which are turned towards each other, which have inclined external side surfaces, and which between them define a groove 44 for receiving an entrainment heel 45 moulded with the cartridge. Also slidably mounted in the above-mentioned groove is a slidable bolt member 46 which is disposed in alignment with the longitudinal member 40 and which is normally in abutment against the end of the groove.

The arm 3 is of an elbow-bent configuration and is pivoted at its elbow onto the body 1, at pivot 47. The arms 2 and 3 of the apparatus are pivotally connected together at their ends at pivot 48, while the first arm is normally urged towards its open or outward position by a spring 49, the second arm being urged towards its closed or inward position by a spring 50. Three connecting links 51, 52 and 53 which are pivoted together in the form of a star are pivoted respectively on the arm 2, the longitudinal member 40 and the slidably bolt member 46, the arrangement being such that a compression force applied to the arm 2 causes the longitudinal member 40 to slide towards the left in FIG. 2a, also producing a force on the slidable member 46 towards the right. However, the member 46 cannot be displaced as it is in abutment against the end of the groove. A rod 54 which is substantially longitudinally directed connects the plate member 46 to the pivot 48 of the levers 2 and 3. The arm 2 carries a lug 55 which is capable of pawl-like engagement in the recess 56 of a pawl 57 loaded by a spring 58. The function of the pawl 57 is to oppose the return movement of the arm 2 to its initial position, once that it has been moved inwardly. Obviously, other mechanisms capable of producing the same movements can be envisaged by the man skilled in the art.

The mode of operation of the above-described apparatus will now be described.

Figure 2A:
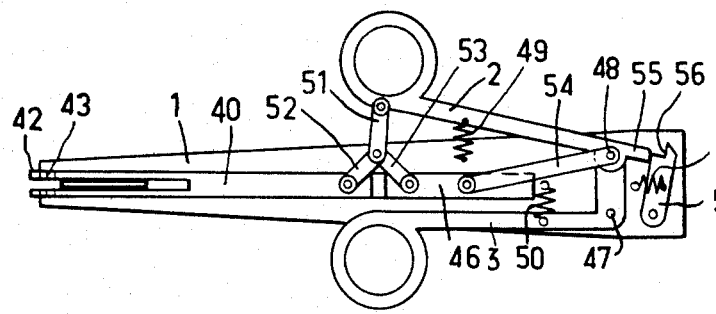

The apparatus is initially in the position shown in FIGS. 1 and 2a. The charger 5, filled with fresh cartridges 8, is set in place and locked onto the apparatus, and the end member 7 is connected to the vacuum conduit in order to create a permanent suction force at the forward end of the tubular shaft 6. A test operation is carried out in order to ensure that a cartridge is properly engaged with the groove 44 by means of its heel 45. The train of cartridges then occupies the position shown in FIGS. 5a and 6a.

The forward end of the apparatus is then applied to the zone surrounding the blood vessel to be ligatured. A bud-shaped portion of tissue 17 is then drawn into the interior of the leading cartridge 8 which projects slightly beyond the tubular shaft 6. The arm 2 is then progressively compressed. In a first phase of such movement, the links 51 to 53 urge the longitudinal member 40 towards the left in FIG. 2a, by a distance $d_1$ (FIG. 3), until reaching the dead point position in which the pivot of the link 51 to the links 52 and 53 is aligned with the links 52 and 53. This movement of the longitudinal member 40 has several effects:

- the lug 55 of the arm 2 (FIG. 2b) engages into the recess 56 of the pawl 57 so that, even if the arm 2 were to be released inadvertently, it would remain in its position in which it has been partially moved inwardly;

- the leading cartridge 8 (FIG. 6a) is driven by the hook 43 of the longitudinal member 40 over the distance $d_1$. During this movement the transverse portions such as 19' of the strands 18 and 19 (FIGS. 3 and 5a) are intercepted by the abutments 25 of the charger, which causes the knot 12 to be tightened around the portion of tissue 17 (FIG. 6b). Simultaneously, the lugs 33 and 34 of the arm 32 (FIG. 3) are engaged by the inclined ramp surfaces 35 and 36 of the charger so that the arm 32 is progressively raised as the cartridge 8 is moved forwardly, and so that the claw member 30 is disengaged from the recess 31 of the following cartridge 8' (FIGS. 5b and 6b);

- the following cartridge 8' comes into engagement, by way of its heel 45, with a pawl member 60 carried by a resilient arm 61 pivoted on the body 1 of the apparatus.

Figure 2B:
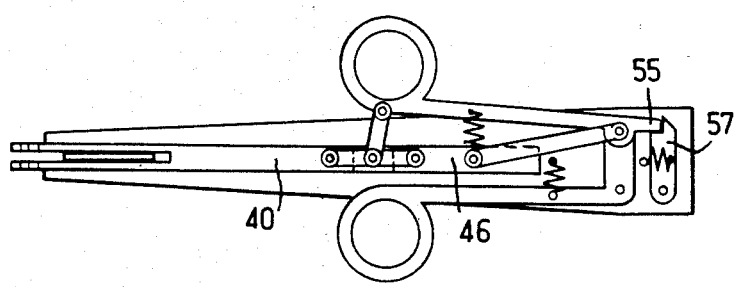
Figure 2C:
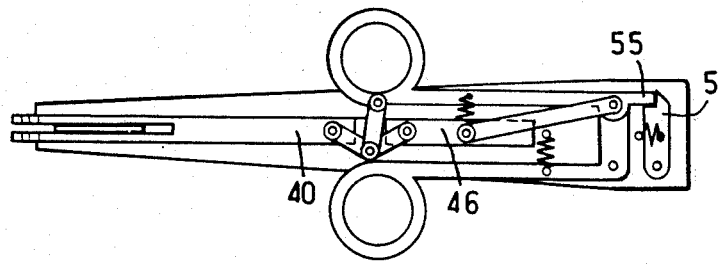
Figure 2D:
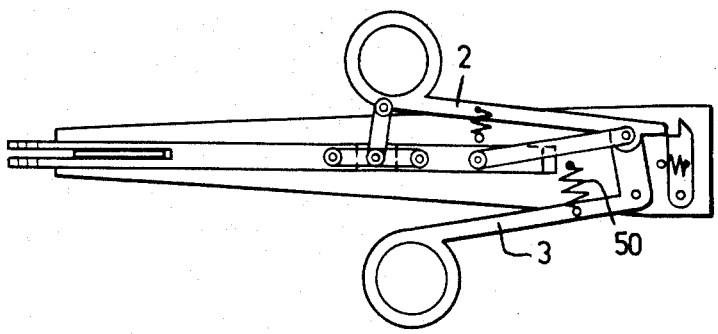

If movement of the arm 2 inwardly of the apparatus is continued beyond the dead point position shown in FIG. 2b, the longitudinal member 40 begins a return movement (FIG. 2c) over a distance $d_2$ which is less than $d_1$; during this movement the leading cartridge 8 is entrained by the hook 42 into abutment against the following cartridge 8' which is held stationary by the pawl member 60 (FIGS. 5c and 6c). There then occurs a sliding movement of the blades 26 and 27 in the guide slides 28 and consequently, the strands 18 and 19 of the knot are cut (FIG. 5c).

Finally, the arm 3 of the apparatus is opened (FIG. 2d), which causes the assembly of the members 40 and 46 to be slid towards the left over a distance $d_3$ which is greater than distance $d_2$. It will be noted that the total elongation of the longitudinal member 40 is then equal to $d = d_1 + d_3 - d_2$, which is greater than $d_1$. At the end of this movement the leading cartridge is ejected from the charger.

As soon as the opening force on the arm 3 is relaxed, the arm 3 is returned by the spring 50 to its initial position, this being possible because the pawl member 57 is pivoted on the body of the apparatus. In this way the longitudinal member 40 returns over the distance $d$, so as to arrive back to its initial position. In this movement the heel 45 of the cartridge 8' engages into the recess 44 of the member 40. The apparatus has then been returned to its initial condition, and is ready for a fresh operation.

It will be appreciated that all the above-described movements are effected sequentially without the danger of error, by virtue of the provision of the pawl member 57 blocking the return movement. These movements are simple and substantially identical to those employed for actuating a haemostatic clamp. Each ligature is effected virtually instantly.

By virtue of the provision of deflection points 20 and 21 (FIG. 3), the tightening forces applied to the strands 18 and 19 of the knot are directed radially outwardly of the knot 12. There is thus the advantage that the force applied is used exclusively for tightening the knot and does not result in a pulling force being applied to the portion of tissue 17, as in cases where such deflection points are not provided.

In addition, the strands of the knot are cleanly cut as such cutting is effected during the return movement of the leading cartridge 8, that is to say, when the strands 18 and 19 are slackened.

As already stated above, the cartridges are disposable. When the charger is empty, it is withdrawn from the apparatus and immediately replaced by a fresh charger which has been prepared beforehand.

I claim:

1. A surgical apparatus for use with knot carrying cartridges and intended for repetitively and instantly making ligatures on blood vessels which are cut, which has substantially the appearance of a haemostatic clamp, comprising a hollow elongate support, slidable means slidably mounted in said support, two arms each having one end pivotally mounted on respective sides of said elongated support and having a ring on the other end for receiving fingers of a user and including means for actuating said slidable means, a hollow elongate charger removably fixed within said elongate support said charger and support being complimentary to each other said charger including a tubular shaft having knot-carrier cartridges slidably mounted thereon that are threaded with a small clearance thereonto, said tubular shaft being arranged co-axially within said charger and connected by its rearward end to a vacuum source so that a suction force will be created at its front end, said charger including at its front end a cartridge disengaging means, each said cartridge comprising a single tubular part having a front end and deflection points diametrically opposed adjacent said front end and carrying a preformed knot within said tubular portion adjacent the front end, which is initially loose, and whose strands extend radially in opposite directions, and bear against said deflection points each of said strands coextending said cartridge to a point adjacent the rear end thereof, each of said strands coextending from said point in a direction transverse with respect to the axial direction of the cartridge, defining a catching portion thereof, each of said strands extending from said catching portion and being fixed on an anchoring portion of the cartridge, each cartridge including two slidable blades, one slidably mounted on each side of said cartridges and extending from the rear end thereof, the front portion of said blade for cutting the strands of the knot at the level of the radially directed portions of the strands, cooperating coupling means and disengagement means extending from the rear end of said cartridges beyond said cutting blades by means of which each cartridge is removably coupled to the preceding and the following cartridges so that the train of cartridges can be displaced as a group, and a heel on each said cartridge at the rear end thereof, gripping means mounted on said sliding means for gripping said heel when the corresponding cartridge arrives at the front end of the charger, link means connected between said arms and said slidable means for movement thereof in an alternating longitudinal movement which includes a first advance movement in the course of which said disengagement means provided on each cartridge and said disengaging means at the front end of the charger disengage the first cartridge of the train, or leading cartridge, from the following cartridge, and abutments on the front end of the charger to intercept the transverse catching portions of the strands, thereby tightening the knot, said link means further providing a first return movement of the leading cartridge so that its said respective cutting blades come into abutment with the following cartridge and are caused to slide from a retracted position to a cutting position to cut the strands of the tightened knot, a second advance movement in the course of which the leading cartridge is expelled from the charger, and a second return movement at the end of which the apparatus returns to its initial condition, the second cartridge assuming the position of the cartridge which had been expelled.

2. Apparatus according to claim 1 wherein each cartridge is provided with a recess and comprises a flexible arm carrying a claw member intended to engage into the recess formed on the following cartridge.

3. Apparatus according to claim 2 wherein the disengagement means comprise two lateral lugs formed on the flexible arm and said disengaging means comprises two ramp surfaces which are inclined upwardly and forwardly and which are formed on the wall of the charger at the forward end, the relative arrangement of the lugs and the ramp surfaces being such that the latter are capable of intercepting the lugs during the movement of the leading cartridge towards the forward end of the charger and resiliently lifting the flexible arm relative to the cartridge, thereby disconnecting the claw member of the leading cartridge from the recess of the following cartridge.

4. Apparatus according to claim 1 wherein said slidable means includes a longitudinal member mounted slidably along said elongate support under the action of the arms thereof and which is terminated at the level of the forward end of the charger by said gripping means, and said gripping means includes two hooks which are turned one towards the other so as to define therebetween a groove for receiving said heel.

5. Apparatus according to claim 4 wherein one of the arms is normally in a position which is spaced away from said support and the other arm is in a position in which it is towards said support, and said link means includes a link assembly connecting the arms to the longitudinal member, first spring means connected with said first arm in such a way that a compression movement of the first arm against said first spring means is converted into said first advance movement, then into said first return movement of the leading cartridge which is entrained by the gripping means, second spring means connected with said second arm that a movement of the second arm away from the body against said second spring means is converted into said second advance movement, and that the return movement of the second arm to its position towards the body returns the longitudinal member to the inwardly displaced position.

6. Apparatus according to claim 5 including pawl means coupled to said elongate support for preventing the first arm from returning to its initial position after it has been moved inwardly towards the body.

7. Apparatus according to claim 1 wherein the knot preferably comprises at least two loops and is secured by hitches for preventing spontaneous undoing of the knot.

* * * * *